United States Patent [19]
Kruse et al.

[11] Patent Number: 5,202,246
[45] Date of Patent: Apr. 13, 1993

[54] TREATMENT OF IMMOBILIZED MATRICES FOR PREPARATION OF PHARMACEUTICAL AND BIOLOGICAL PRODUCTS WITH ANTI-MICROBIAL AGENTS TO REMOVE PYROGEN-PRODUCING ORGANISMS AND PYROGENS

[75] Inventors: Robert Kruse; Sudhish Chandra, both of Bourbonnais; Fred Feldman, Park Forest, all of Ill.

[73] Assignee: Armour Pharmaceutical Company, Collegeville, Pa.

[21] Appl. No.: 798,255

[22] Filed: Nov. 18, 1991

Related U.S. Application Data

[63] Continuation of Ser. No. 395,115, Aug. 16, 1989, abandoned.

[51] Int. Cl.$^5$ .................. C12N 11/00; C07K 17/02; B01D 15/08; A61K 35/14
[52] U.S. Cl. ..................... 435/174; 435/176; 435/177; 530/380; 530/383; 530/391.1; 530/389.3; 530/413; 530/416; 424/94.3; 424/530; 210/656; 210/679; 210/692

[58] Field of Search ............. 424/530, 94.3; 210/656, 210/679, 692; 530/810–812, 380, 383, 387; 435/174, 176, 177

[56] References Cited

U.S. PATENT DOCUMENTS

| | | | |
|---|---|---|---|
| 4,000,257 | 12/1976 | Cano | 424/89 |
| 4,147,592 | 4/1979 | Bai et al. | 424/530 |
| 4,315,919 | 2/1982 | Shanbrom | 424/530 |
| 4,380,511 | 4/1983 | Mannuzza et al. | 424/530 |
| 4,381,239 | 4/1983 | Chibata et al. | 210/679 |
| 4,481,189 | 11/1984 | Prince | 424/530 |
| 4,673,733 | 6/1987 | Chandra et al. | 424/530 |
| 4,774,323 | 9/1988 | Neuman et al. | 530/414 |
| 4,841,023 | 6/1989 | Horowitz | 424/529 |
| 4,939,176 | 7/1990 | Seng et al. | 530/381 |

Primary Examiner—Jacqueline Stone
Attorney, Agent, or Firm—Martin F. Savitzky; Rosanne Goodman; Raymond S. Parker

[57] ABSTRACT

Disclosed are methods of inactivating pyrogen producing organisms and pyrogenic substances in immobilized solid matrices which are used in the production and/or purification of biomedical and pharmaceutical products and materials by contacting the solid matrices with pyrogen inactivating solutions.

41 Claims, No Drawings

TREATMENT OF IMMOBILIZED MATRICES FOR PREPARATION OF PHARMACEUTICAL AND BIOLOGICAL PRODUCTS WITH ANTI-MICROBIAL AGENTS TO REMOVE PYROGEN-PRODUCING ORGANISMS AND PYROGENS

This is a continuation of co-pending application Ser. No. 07/395,115 filed on Aug. 16, 1989, now abandoned.

BACKGROUND OF THE INVENTION

1. Field of the Invention

This invention relates to a method of reducing pyrogenicity of immobilized matrices used in the production and/or purification of biological and pharmaceutical products. More particularly, the invention relates to a method of inactivating pyrogens which contaminate immobilized matrices used in the production and/or purification of biological and pharmaceutical products by contacting the matrices in a packed bed configuration with a pyrogen inactivating solution.

2. Description of the Prior Art

Pyrogens are lipopolysaccharides, also known as endotoxins, which are an integral component of the outer cell surface of gram-negative bacteria. The pyrogens are shed from living bacteria and also are released into the environment when bacteria die and decompose. Since gram-negative bacteria are found universally in air, water and soil, bacterial endotoxins commonly contaminate the raw materials used to produce biological and pharmaceutical products as well as the processing systems and equipment used in the production of such products.

Pyrogens have numerous biological activities which include the production of fever, activation of clotting mechanisms and induction of shock. Consequently, it is essential that causative bacteria be inactivated in, and pyrogenic substances removed from, biological and pharmaceutical products as well as from the processing systems and equipment used in the production of the products.

Inactivation of pyrogens in products, processing systems and equipment, in general, includes: acid and base hydrolyses coupled with heat treatment; oxidation by hydrogen peroxide; alkylation by acetic anhydride, succinic anhydride and ethylene oxide; treatment with dry and moist heat and ionizing radiation. Removal of pyrogens include: rinsing equipment or materials with water; distillation; ultrafiltration; adsorption to activated carbon and removal by affinity chromatography. Methods of inactivation and removal of pyrogens must be compatible with the particular product and/or equipment and should not adversely affect the same while eliminating the pyrogenic substances. For example, while dry heat treatment destroys pyrogens, it is not suitable for heat-sensitive items, such as most polymerics, aqueous solutions and thermolabile biological agents. Wet heat, on the other hand, up to autoclave temperatures, does not destroy pyrogens, although it kills the organisms responsible for their production. Depyrogenation by the use of certain chemicals is also undesirable. For example, pyrogens are destroyed by sodium hydroxide at pH values greater than 8.0, but such high pH's are incompatible with various pharmaceutical processes as well as some products. Specifically: silicon based chromatography matrices dissolve; magnesium surfaces are violently attacked; and sensitive biological molecules tend to be unstable under these conditions.

The present invention is directed to the depyrogenation of solid matrices that are used in the processing of certain pharmaceutical/biological materials in order to prevent pyrogen-producing organisms and pyrogens produced thereby from entering into the process stream and products. Specific prior art methods and procedures do not relate to such depyrogenation and the general methods for depyrogenating products, equipments and raw materials are less than satisfactory to achieve Applicants' objectives.

SUMMARY OF THE INVENTION

It has now been discovered that pyrogen producing organisms and/or pyrogenic substances may be removed from immobilized matrices by methods I, II and III described hereunder.

Method I comprises the steps of:

a) Packing a column with the desired chromatography matrix;

b) Equilibrating the column with a buffer solution having a pH of about 6.0 to 8.0, and preferably of about 6.8 to 7.2;

c) Treating the immobilized matrix by contacting the same with a pyrogen inactivating aqueous solution, having a pH of about 2.0 to 6.0 and preferably of about 3.2 to 3.6, consisting of about 0.1M to 1.5M of an inorganic salt selected from the group consisting of sodium chloride, potassium chloride, calcium chloride, barium chloride and magnesium chloride; and about 0.15M to 1.0M of an organic acid selected from the group consisting of saturated and unsaturated fatty acids having from 1 to 10 carbon atoms; and d) Re-equilibrating the matrix by the buffer solution used in step b) to render the column ready for use to treat biological and/or pharmaceutical raw materials and/or products.

Method II comprises the steps of:

a) Packing a column with the desired chromatography matrix;

b) Equilibrating the column with a buffer solution having a pH of about 6.0 to 8.0, and preferably of about 6.8 to 7.2;

c) Treating the immobilized matrix by contacting the same with a pyrogen inactivating buffer solution, having a pH of about 3.2 to 7.2, consisting of about 0.1M to 2.0M of an inorganic salt selected from the group consisting of sodium chloride, potassium chloride, calcium chloride, barium chloride and magnesium chloride; about 0.15M to 1.0M of an organic acid selected from the group consisting of saturated and unsaturated fatty acids having up to 10 carbon atoms; about 10 mM to 50 mM of L-histidine and; about 50 mM to 200 mM L-lysine monohydrochloride; and d) Re-equilibrating the matrix by the buffer solution used in step b) to render the column ready for use to treat biological and/or pharmaceutical raw materials and/or products.

Method III comprises the steps of:

a) Packing a column with the desired chromatography matrix;

b) Equilibrating the column with a buffer solution having a pH of about 6.0 to 8.0, and preferably of about 6.8 to 7.2;

c) Treating the immobilized matrix by contacting the same with a pyrogen inactivating aqueous solution, having a pH of about 8.0 to 11.0, consisting of about 0.1M to 1.5M of an inorganic salt selected from the group consisting of sodium chloride, potassium chloride, calcium chloride, barium chloride and magnesium chloride; and about 0.01M to 0.7M sodium hydroxide, magnesium hydroxide, calcium hydroxide, barium hydroxide and ammonium hydroxide; and d) Re-equilibrating the matrix by the buffer solution used in step b) to render the column ready for use to treat biological and/or pharmaceutical raw materials and/or products.

These embodiments of the present invention were found to drastically reduce pyrogen producing organisms and/or pyrogens in immobilized matrices as will be further described in the specification.

DETAILED DESCRIPTION OF THE INVENTION

The depyrogenating process of the present invention is applicable to a variety of solid matrices in a packed bed or column configuration widely used in the production, separation and purification of products intended for therapeutic use in the human or animal body for biomedical or therapeutic purposes, as well as non-therapeutic experimental purposes. These biomedical products and materials include but are not limited to: blood fractions such as Antihemophilic Factor (AHF, Factor VIII), prothrombin complex (Factors II, VII, IX and X), individual or groups of Factor II, Factor VII, Factor IX, Factor X, Protein C, Antithrombin III, C-1 Esterase Inhibitor, Fibronectin, Gamma Globulin and Albumin derived from human or animal origin; biological and pharmaceutical products derived from animal origin; e.g., insulin, enzymes, coenzymes, antibodies and hormones, and biological products derived from human or animal placentae, e.g., blood fractions, and vaccines.

As used herein, the solid matrix or solid phase is meant to define a substance used as an ion exchanger, resins used for affinity chromatography, resins with an attached antibody against the particular or related antigen, special membrane media which act as an ion exchanger or are capable of adsorbing particular substances, or glass beads which are treated to produce surfaces that act as an ion exchanger or affinity resin. Contemplated solid matrix or solid phase materials include:

a) An ion exchanger, e.g., DEAE Sephadex, QAE Sephadex, CM-Sephadex, SP-Sephadex, DEAE Biogel A, CM Biogel A, Biogel HTP, DEAE Cellulose;

b) Resins used for affinity chromatography, such as Sepharose 2B, Sepharose 4B, Sepharose 6B, Sepharose CL-2B, Sepharose CL-4B and Biogel A-15 with an attached ligand consisting of, for example, an inhibitor, enzyme, coenzyme, or hormone. The attached ligand is capable of adsorbing the biological or pharmaceutical product, for example, heparin attached to a Sepharose resin adsorbs Antithrombin III. The attached ligand may be an antibody to the antigen or related antigen present in the product. An example is antibody to Anti-hemophilic Factor related antigen attached to a Sepharose resin to adsorb Antihemophilic Factor. The attached ligand may also be a monoclonal or polyclonal antibody to the antigen which might be desired to be isolated as the biological or pharmaceutical product;

c) Resins described in b) above with an attached antibody (monoclonal or polyclonal) against a particular antigen or an antigen itself;

d) Special membrane media which act as an ion exchanger, e.g., Zeta-Prep TM cartridge, DEAE, QAE, and SP;

e) Controlled-Pore Glass beads which are treated to produce surfaces that act as an ion exchanger, e.g., DEAE-CPG, CML-CPG; and f) Controlled-Pore Glass beads attached with biologicals of interest such as inhibitors, enzymes, coenzymes, hormones, antibodies, and antigens.

These matrices are well-known, and are available from various commercial sources.

Various buffers may be used in practicing the present invention. One such buffer solution consists of a low molar physiologic buffer such as imidazole, sodium phosphate, HEPES, ammonium bicarbonate, EACA, glycine, or TRIS, although various other similar acting buffers have been found effective. Additional ingredients in the buffer solution might consist of a low molar physiologic salt, such as NaCl, a low molar physiological anticoagulant, such as sodium citrate. We prefer to use the buffer consisting of about 10 mM to 50 mM of L-histidine, about 50 mM to 200 mM L-lysine monohydrochloride and 50 to 300 mM sodium chloride.

The agents used in preparing the depyrogenating solutions and buffers are readily available from commercial supply houses.

The following examples will further illustrate the invention.

EXAMPLE 1

Inhibition of Pyrogen-Bearing Bacteria by the Use of an Aqueous Acid and Salt Solution A chromatography column was packed with the anti-Factor VIII:R Sepharose CL-2B matrix (as described in U.S. Pat. Re. No. 32,011, incorporated herein by reference) which is used in the process of producing ultrapurified Factor VIII using monoclonal antibodies. Next, the column was equilibrated with a pH 7 buffer consisting of 20 mM L-histidine, 100 mM L-lysine monohydrochloride and 150 mM of sodium chloride (hereinafter Factor VIII:C buffer) by pumping the buffer through the column at a rate of one column volume per hour for 3 hours. The column was then treated with the antibacterial solution having a pH of 3.4, consisting of 0.5M sodium chloride and 0.33M glacial acetic acid, by pumping said antibacterial solution through the column at a rate of one column volume per hour. The same treatment was repeated by pumping another column volume through. The column was then re-equilibrated by washing the same with the Factor VIII:C buffer at a rate of one column volume per hour for 3 column volumes. (Monitoring the effluent for pH allows one to determine when the column returns to equilibrium.) The effluent was also monitored for endotoxin using the Limulus Amoebocyte Lysate Test (LAL), while the Total Aerobic Microbial Count Test was used to determine the total number of aerobic bacteria in a sample. Both tests are described hereunder.

The Limulus Lysate Test

The test is designed to detect the presence of small concentrations of endotoxin. The endpoint of the test is the formation of a firm gel when lysate is incubated with an endotoxin.

It is important that all equipment, such as glassware and pipettes, must be made pyrogen free and the reaction be conducted under neutral pH range, i.e., 6.75 to 7.5.

Materials needed for the test are as follows:

1) Lyopholized lysate 10 to 50 test size having a specific endotoxin sensitivity of 0.125 Eu/ml (Endotoxin units/ml). (A test kit is obtainable from commercial suppliers, such as, Associates of Cape Cod, Inc.) The lyophilized lysate is reconstituted with sterile water for injection according to the instruction on vial label.

2) Endotoxin Standard, either U.S.P. Reference Standard Endotoxin (RSE) or Control Standard Endotoxin (CSE) standardized against U.S.P., is reconstituted by adding vial label indicated amount of sterile water for injection.

3) Positive Endotoxin Control is prepared by diluting the standard (step 2) with sterile water so as to obtain a two-fold dilution series containing five concentrations which bracket the sensitivity of the test lysate.

4) Pyrogen free water is used for negative control.

5) A positive Sample Control is prepared by diluting the Endotoxin Standard with a test sample so as to obtain a concentration of endotoxin equal to twice the labeled lysate sensitivity, and a test sample dilution equal to that being tested ($\lambda$=lysate sensitivity).

6) Serial dilutions are prepared by diluting a sample with sterile water so that each subsequent dilution contains twice the volume of the sterile water used in the previous dilution (i.e., 1:1, 1:2, 1:4, 1:8 and 1:16).

The test procedure is as follows:

a) 0.1 ml of the Positive Endotoxin Controls and 0.1 ml of the Positive Sample Controls (steps 3 and 5) are added to duplicate series of pyrogen free tubes.

b) 0.1 ml of the Negative Control is added to each of two pyrogen free tubes.

c) 0.1 ml of the Positive Sample Control is added to each of two pyrogen free tubes.

d) 0.1 ml of the various dilutions of the test samples are added to two series of pyrogen free tubes.

e) 0.1 ml of the reconstituted lysate (step 2) is added to all tubes and the tubes are placed in a water bath in which a constant temperature of 37° C. ±0.5° C. is maintained.

f) After gentle mixing, the mixtures are incubated for one hour at 37° C.±0.5° C.

g) The endpoint is read by inverting the tubes 180°. If a gel is formed in the bottom of a tube, which remains in place upon inversion, the test is considered positive. Contrarywise, if no gel is formed or a weak gel is formed which breaks upon inversion, the test is considered negative.

h) The concentration of endotoxin is calculated by the formula: pS/U where
p=predilution factor for the test specimen;
S=antilog of the geometric mean $\log_{10}$ of the endpoint expressed in Eu/ml for the standard endotoxin; and
U=antilog of $$\frac{\Sigma_e}{f},$$

where e is the $\log_{10}$ of the endpoint dilution factors expressed in decimal fractions and f is the number of replicate reaction tubes.

The Total Aerobic Microbial Count Test

The method is used for enumerating total aerobic bacteria contained in a solid or liquid sample. Varying amounts of a sample, dispersed in a buffer solution, are mixed with liquid soybean-casein digest agar. The solidified plates are incubated at 32° C. for 48-72 hours and the average number of colonies is expressed per gram, or ml, of the sample.

Materials used are as follows:

1) Soybean-Casein Digest Agar Medium U.S.P. or equivalent commercially available dehydrated mixtures.

2) 4% NaOH.

3) Phosphate Buffer, pH 7.2 Stock Solution: 34 gms of monobasic potassium phosphate is dissolved in approximately 500 ml of purified water. The pH is adjusted to 7.2±0.1 by adding 175 ml of a 4% sodium hydroxide solution. Then sufficient water is added to make 1,000 ml of the solution which is then sterilized at 121° C. for 15 minutes.

4) Working Phosphate Buffer: The Stock Phosphate Buffer solution is diluted with water in the ratio of 1 to 800, then sterilized at 121° C. for 15 minutes.

The test procedure is as follows:

a) 2.2 ml of an undiluted liquid sample is removed and 0.1 ml, 0.1 ml, 1.0 ml and 1.0 ml aliquots are transferred into Petri dishes.

b) 10 g, or 10 ml of liquid, of test material is transferred to a dilution bottle containing 90 ml of the Working Phosphate Buffer (dilution 1:10) and mixed thoroughly.

c) 2.2 ml of the mixture in b) is removed and 0.1 ml, 0.1 ml, 1.0 ml and 1.0 ml aliquots are dispensed into Petri dishes (1:100 and 1:10 dilution).

d) 1 ml of the 1:10 dilution (from step c) is transferred to a second dilution bottle containing 99 ml of the Working Phosphate Buffer and mixed thoroughly (dilution 1:1000).

e) 2.2 ml of the 1:1,000 dilution (step d) is removed and 0.1 ml (1:10,000) and 1.0 ml (1:1,000), each in duplicate, is pipetted into Petri dishes.

f) 1.0 ml of the 1:1000 dilution (step c) is transferred to a third dilution bottle containing 99 ml of the Working Phosphate Buffer and mixed thoroughly (1:100,000).

g) From the 1:100,000 dilution (step f) 2.2 ml is removed and 0.1 ml and 1.0 ml, each in duplicate, are added to Petri dishes (1:1,000,000 and 1:100,000).

h) Approximately 20 ml of the Soybean-Casein Digest Agar Medium U.S.P. at a temperature of about 45° C. is added to each of the Petri dishes, swirled to mix and the mixture is allowed to solidify.

i) The plates are inverted to avoid condensation and are incubated at 30°-35° C. for 48-72 hours.

j) Finally, the plates are examined for growth: the number of colonies are counted and the result expressed in terms of number of microorganisms per gram, or ml, of sample.

A contaminated anti-Factor VIII:R-sepharose CL-2B resin was treated with the depyrogenating solution consisting of 0.33M acetic acid and 0.5M sodium chloride. Samples were withdrawn at six hour intervals and tested for bio-burden. Result showing colony forming units/gm is shown in Table I.

TABLE I

Reduction of Microorganisms in contaminated Anti-Factor VIII:R-Sepharose CL-2B Resin Colony Forming Units/Gram of Sepharose Resin Through Exposure Time

| TIME (hrs) | CONTROL | NaCL-HAc |
|---|---|---|
| 0 | 213,000 | 213,000 |
| 6 | 199,000 | 370 |
| 12 | 226,000 | 360 |
| 18 | 244,000 | 720 |

TABLE I-continued

Reduction of Microorganisms in contaminated
Anti-Factor VIII:R-Sepharose CL-2B Resin
Colony Forming Units/Gram of Sepharose Resin
Through Exposure Time

| TIME (hrs) | CONTROL | NaCL-HAc |
|---|---|---|
| 24 | 252,000 | 390 |

EXAMPLE 2

The method of Example 1 was used to test the effectiveness of depyrogenating solutions in which the concentrations of the depyrogenating agents were varied as well as the duration of time the samples were subjected to the action of the depyrogenating solutions. The formulations tested were as follows:

A = Factor VIII:C buffer solution as control
B = 0.5M sodium chloride +0.33M acetic acid
C = 0.5M sodium chloride +0.83M acetic acid
D = 2M sodium chloride +0.33M acetic acid
E = 2M sodium chloride +0.83M acetic acid
Results are shown in Table II

TABLE II

Reduction of MAb Resin Microbial Load with Different Formulations of NaCl and HAc in Factor VIII:C Buffer

| Sample Time | A | B | C | D | E |
|---|---|---|---|---|---|
| 0 min. | $102 \times 10^7$ | $158 \times 10^7$ | $75 \times 10^7$ | $122 \times 10^7$ | $127 \times 10^7$ |
| 1 min. | $102 \times 10^7$ | $10 \times 10^5$ | $10 \times 10^5$ | $70 \times 10^5$ | $3 \times 10^5$ |
| 60 min. | $127 \times 10^7$ | $31 \times 10^3$ | 100 | $33 \times 10^3$ | $2 \times 10^2$ |
| 120 min. | $90 \times 10^7$ | <100 | <100 | $16 \times 10^3$ | <100 |

Numbers are viable counts per ml of resin slurry. Numbers not differing by more than 1 power of 10 are not significantly different. Numbers less than 100 are too low to count.

EXAMPLE 3

Two column volumes of a depyrogenating solution, consisting of 2% w/v acetic acid and 0.5M sodium chloride formulated in Factor VIII:C buffer, was pumped through a chromatography column containing anti-factor VIII:R Sepharose CL-2B affinity resin. The flow rate was one column volume per hour, and was followed by factor VIII:C buffer, which was pumped in at the same rate to re-equilibrate the column for the next run. Thirteen different columns have received this treatment multiple times over a period of 8 months in a production setting. There has been no evidence of adverse reactions to equipment, Sepharose resin, or the coupling between the antibody and the resin.

The columns were also tested (limulus Amoebocyte Lysate Assay) for the presence of endotoxin before and after treatment with the depyrogenating solution. Results are shown in Table III.

TABLE III

Reduction in Endotoxin in Sepharose CL-2B Resins

| Column | Endotoxin units/ml Before | After |
|---|---|---|
| A | 16.0 | 0.5 |
| B | 1.0 | 0.25 |
| C | 4.0 | 1.0 |
|   | 16.0 | 0.25 |
| D | 4.0 | 1.0 |
|   | 1.0 | 0.25 |
| E | 8.0 | 0.5 |
|   | 4.0 | 2.0 |

TABLE III-continued

Reduction in Endotoxin in Sepharose CL-2B Resins

| Column | Endotoxin units/ml Before | After |
|---|---|---|
| F | 8.0 | 4.0 |
|   | 0.5 | 0.125 |
| G | 8.0 | 0.25 |
|   | 32.0 | 0.25 |
|   | 256.0 | 4.0 |

EXAMPLE 4

Treatment of a Biogel HTP solid matrix using a depyrogenating solution of 1.0M NaCl and 0.5M NaOH can deyrogenate the resin in comparable fashion to the results shown in Table III.

It will be appreciated by those skilled in the art that the present invention will greatly improve the processing of biomedical products and materials by providing solid matrices practically free from pyrogens and pyrogen producing microorganisms.

It should also be understood by those skilled in the art that various modifications may be made in the present invention without departing from the spirit and scope thereof as described in the specification and defined in the appended claims.

What is claimed is:

1. A method of depyrogenating immobilized matrices comprising the steps of:
    contacting the immobilized solid matrix with a pyrogen inactivating aqueous solution for a time sufficient to inactivate pyrogen producing microorganisms and pyrogenic substances, said pyrogen inactivating aqueous solution consisting of about 0.1M to 1.5M of an inorganic salt selected from the group consisting of sodium chloride, potassium chloride, calcium chloride, barium chloride and magnesium chloride, and about 0.15M to 1.0M of an organic acid selected from the group consisting of saturated and unsaturated fatty acids having from 1 to 10 carbon atoms; and
    washing said immobilized solid matrix with a buffer solution having a pH of about 6.0 to 8.0.

2. The method of claim 1 wherein said solid matrix is an ion exchanger resin.

3. The method of claim 1 wherein said solid matrix is an affinity resin having attached thereto a ligand capable of adsorbing biological or pharmaceutical products.

4. The method of claim 3 wherein said ligand is selected from the group consisting of an inhibitor, enzyme, coenzyme or hormone.

5. The method of claim 4 wherein said ligand is heparin.

6. The method of claim 1 wherein said solid matrix is an affinity resin having attached thereto a monoclonal or polyclonal antibody.

7. The method of claim 6 wherein said antibodies are antibodies to Antihemophilic Factor antigen.

8. The method of claim 1 wherein said solid matrix is controlled-pore glass beads adapted to produce ion exchange or affinity effect.

9. The method of claim 8 wherein said controlled-pore glass beads are treated with an agent capable of adsorbing biological or pharmaceutical products, said agent is selected from the group consisting of an inhibitor, enzyme, coenzyme, hormone, antibody or antigen.

10. The method of claim 1 wherein said solid matrix is a synthetic membrane adapted to produce ion exchange or affinity effect.

11. The method of claim 10 wherein said synthetic membrane is treated with an agent capable of adsorbing biological or pharmaceutical products, said agent is selected from the group consisting of an inhibitor, enzyme, coenzyme, hormone, antibody or antigen.

12. The method of claim 1 wherein said buffer solution contains about 10 mM to 50 mM L-histidine, about 50 mM to 200 mM of L-lysine monohydrochloride, and about 50 mM to 300 mM of sodium chloride.

13. The method of claim 1 wherein said pyrogen inactivating aqueous solution is at a pH of about 2.0 to 6.0.

14. The method of claim 1 wherein said pyrogen inactivating aqueous solution is at a pH of about 3.2 to 3.6.

15. The method of claim wherein said solid matrix is washed with said pyrogen inactivating aqueous solution.

16. A method of depyrogenating solid matrices comprising the steps of:
contacting the immobilized solid matrix with a pyrogen inactivating buffer solution for a time sufficient to inactivate pyrogen producing microorganisms and pyrogenic substances, said pyrogen inactivating buffer solution, having a pH of about 3.2 to 7.2, consisting of about 0.1M to 2.0M of an inorganic salt selected from the group consisting of sodium chloride, potassium chloride, calcium chloride, barium chloride and magnesium chloride, and about 0.15M to 1.0M of an organic acid selected from the group consisting of saturated and unsaturated fatty acids having from 1 to 10 carbon atoms, and about 10 mM to 50 mM of L-histidine, 50 mM to 200 mM L-lysine monohydrochloride; and
washing said immobilized solid matrix with a second buffer solution having a pH of about 6.0 to 8.0.

17. The method of claim 16 wherein said solid matrix is an ion exchanger resin.

18. The method of claim 16 wherein said solid matrix is an affinity resin having attached thereto a ligand capable of adsorbing biological or pharmaceutical products.

19. The method of claim 18 wherein said ligand is selected from the group consisting of an inhibitor, enzyme, coenzyme or hormone.

20. The method of claim 19 wherein said ligand is heparin.

21. The method of claim 16 wherein said solid matrix is an affinity resin having attached thereto a monoclonal or polyclonal antibody.

22. The method of claim 21 wherein said antibody is antibody to Antihemophilic Factor antigen.

23. The method of claim 16 wherein said solid matrix is controlled-pore glass beads adapted to produce ion exchange or affinity effect.

24. The method of claim 23 wherein said controlled-pore glass beads are treated with an agent capable of adsorbing biological or pharmaceutical products, said agent is selected from the group consisting of an inhibitor, enzyme, coenzyme, hormone, antibody or antigen.

25. The method of claim 16 wherein said solid matrix is a synthetic membrane adapted to produce ion exchange or affinity effect.

26. The method of claim 25 wherein said synthetic membrane is treated with an agent capable of adsorbing biological or pharmaceutical products, said agent is selected from the group consisting of an inhibitor, enzyme, coenzyme, hormone, antibody or antigen.

27. The method of claim 16 wherein said second buffer solution contains about 10 mM to 50 mM of L-histidine, about 50 mM to 200 mM of L-lysine monohydrochloride, and about 50 mM to 300 mM of sodium chloride.

28. The method of claim 16 wherein said solid matrix is washed with said pyrogen inactivating buffer solution.

29. A method of depyrogenating solid matrices comprising the steps of:
contacting the immobilized solid matrix with a pyrogen inactivating aqueous solution having a pH of about 8.0 to 11.0 for a time sufficient to inactivate pyrogen producing microorganisms and pyrogenic substances, said pyrogen inactivating aqueous solution consisting of about 0.1M to 1.5M of an inorganic salt selected from the group consisting of sodium chloride, potassium chloride, calcium chloride, barium chloride and magnesium chloride, and about 0.01M to 0.7M of an inorganic base selected from the group consisting of sodium hydroxide, magnesium hydroxide, calcium hydroxide, barium hydroxide and ammonium hydroxide; and
washing said immobilized solid matrix with a buffer solution having a pH of about 6.0 to 8.0.

30. The method of claim 29 wherein said solid matrix is an ion exchanger resin.

31. The method of claim 29 wherein said solid matrix is an affinity resin having attached thereto a ligand capable of adsorbing biological or pharmaceutical products.

32. The method of claim 31 wherein said ligand is selected from the group consisting of an inhibitor, enzyme, coenzyme or hormone.

33. The method of claim 32 wherein said ligand is heparin.

34. The method of claim 29 wherein said solid matrix is an affinity resin having attached thereto a monoclonal or polyclonal antibody.

35. The method of claim 34 wherein said antibody is antibody to Antihemophilic Factor antigen.

36. The method of claim 29 wherein said solid matrix is controlled-pore glass beads adapted to produce ion exchange or affinity effect.

37. The method of claim 36 wherein said controlled-pore glass beads are treated with an agent capable of adsorbing biological or pharmaceutical products, said agent is selected from the group consisting of an inhibitor, enzyme, coenzyme, hormone, antibody or antigen.

38. The method of claim 29 wherein said solid matrix is a synthetic membrane adapted to produce ion exchange or affinity effect.

39. The method of claim 38 wherein said synthetic membrane is treated with an agent capable of adsorbing biological or pharmaceutical products, said agent is selected from the group consisting of an inhibitor, enzyme, coenzyme, hormone, antibody or antigen.

40. The method of claim 29 wherein said buffer solution contains about 10 mM to 50 mM of L-histidine, about 50 mM to 200 mM of L-lysine monohydrochloride, and about 50 mM to 300 mM of sodium chloride.

41. The method of claim 29 wherein said solid matrix is washed with said pyrogen inactivating aqueous solution.

* * * * *